United States Patent
Polat et al.

(10) Patent No.: US 12,207,872 B2
(45) Date of Patent: Jan. 28, 2025

(54) COMPUTERIZED BEHAVIORAL METHOD FOR EYE-GLASSES PRESCRIPTION

(71) Applicant: BAR-ILAN UNIVERSITY, Ramat Gan (IL)

(72) Inventors: Uri Polat, Ramat Gan (IL); Maria Lev, Herzelia (IL); Yoram Bonneh, Hod-Hasharon (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 985 days.

(21) Appl. No.: 17/269,878

(22) PCT Filed: Aug. 19, 2019

(86) PCT No.: PCT/IL2019/050922
§ 371 (c)(1),
(2) Date: Feb. 19, 2021

(87) PCT Pub. No.: WO2020/039426
PCT Pub. Date: Feb. 27, 2020

(65) Prior Publication Data
US 2021/0330181 A1    Oct. 28, 2021

Related U.S. Application Data

(60) Provisional application No. 62/719,717, filed on Aug. 20, 2018.

(51) Int. Cl.
*A61B 3/032* (2006.01)
*A61B 3/036* (2006.01)
*A61B 3/18* (2006.01)

(52) U.S. Cl.
CPC .............. *A61B 3/032* (2013.01); *A61B 3/036* (2013.01); *A61B 3/18* (2013.01)

(58) Field of Classification Search
CPC ............ A61B 3/032; A61B 3/036; A61B 3/18
USPC ....................................................... 351/239
See application file for complete search history.

(56) References Cited

U.S. PATENT DOCUMENTS

| | | | |
|---|---|---|---|
| 4,105,302 A | 8/1978 | Tate, Jr. | |
| 2006/0152675 A1 | 7/2006 | Toshima et al. | |
| 2010/0007850 A1* | 1/2010 | Aggarwala | A61B 3/0091 351/237 |
| 2011/0063571 A1 | 3/2011 | Duffy | |
| 2012/0106813 A1 | 5/2012 | Drobe et al. | |
| 2014/0268060 A1* | 9/2014 | Lee | A61B 3/107 351/241 |
| 2014/0356827 A1 | 12/2014 | Duffy | |
| 2016/0120402 A1 | 5/2016 | Limon | |
| 2017/0188813 A1 | 7/2017 | Arnold et al. | |

FOREIGN PATENT DOCUMENTS

WO    WO-2010117386 A1 * 10/2010 ............. A61B 3/032

* cited by examiner

*Primary Examiner* — James R Greece
(74) *Attorney, Agent, or Firm* — Maschoff Brennan

(57) ABSTRACT

A method for measuring an optical error of a subject comprises displaying to said subject stimuli comprising different levels of blurring.

18 Claims, 11 Drawing Sheets

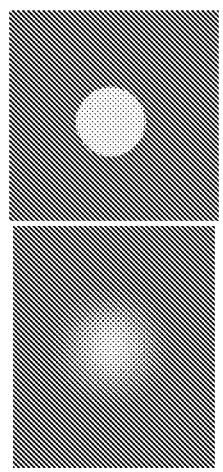
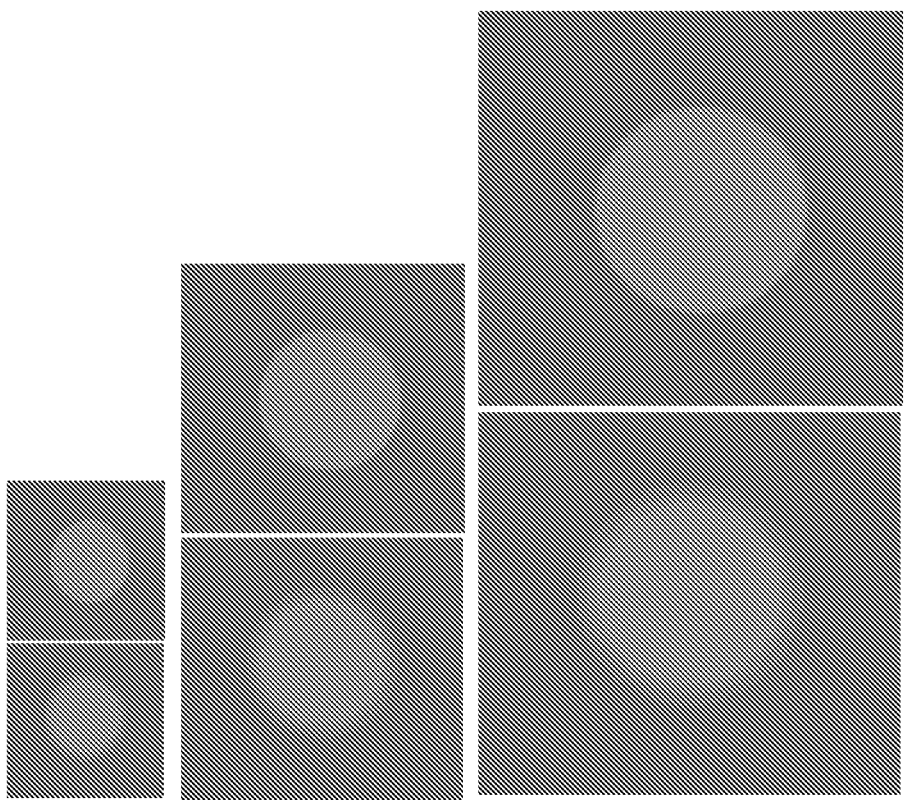
Fig. 5 (a)
Fig. 5 (b)

COMPUTERIZED BEHAVIORAL METHOD FOR EYE-GLASSES PRESCRIPTION

FIELD OF THE INVENTION

The present invention relates to a method for measuring the visual capability of a user. More particularly, the invention relates to a method for generating a prescription for a user's eyewear.

BACKGROUND OF THE INVENTION

Visual Acuity and Optical Error

Normal vision, emmetropia, is a condition in which the parallel light rays coming from an object localized at more than 6 meters away, on the retina on the focus point. This situation is schematically shown in FIG. 1, which also illustrates three abnormal conditions, i.e., myopia, hyperopia, and astigmatism. Refractive error occurs when light is not focused on the retina due to the shape of the eye. The most common types of refractive errors are myopia, hyperopia, astigmatism and presbyopia. Myopia results in the perception of far objects as blurry, due to the fact that the focus point is located before the retina. Hyperopia, on the other hand, results in the perception of close objects as blurry when light is focused after the retina.

Astigmatism is a refractive error, which is due to a deviation from a spherical curvature of the cornea, which results in a distorted image along the astigmatic axis. Thus, the refractive power is different in various meridians and, consequently, there is a meridian with high refractive error and a meridian orthogonal to it, with a weaker refractive error. Therefore, there will be two images on the retina, as schematically illustrated in FIG. 1. The distant object has two focal lines parallel to the meridians of the maximum and minimum power; thus, a point of focus is never formed.

Therefore, when there is a refractive error a blurred image falls on the retina, as schematically illustrated in FIG. 2. In order to bring the object to focus on the retina, thereby avoiding the blur, one needs to apply in optical correction using lenses with a power known as diopter. Diopter is a unit that describes the optical power of a lens, which is equal to the reciprocal of the focal length measured in meters. For example 1 diopter describes a focal point at 1 meter. The clinician's task is to find the best optical correction in diopters, which will minimize the optical error or the optical blur on the retina, and achieve the best visual acuity (VA).

Visual acuity (VA) is the most commonly used measure of human visual function, and is considered the standard measure of visual function in clinical settings. Standard tests of VA measure the ability to identify black symbols on a white background at a standardized distance, as a function of the size of the symbols, such as with one of the familiar eye charts (e.g., Snellen, Bailey-Lovie, Tumbling E, Landolt C, and so forth), the standardized distance being approximately 6 meters or 20 feet. Three examples of such eye charts are shown in FIG. 3. A person with standard (normal) VA can recognize a letter or symbol that subtends an angle of 5 arc minutes. For example, the block letter E, shown in FIG. 4, has three horizontal black strokes plus two interspersed horizontal white spaces of comparable thickness. Normal human visual resolution is nominally 1 arc minute. For angular values of this magnitude, the angle subtended by an object is approximately inversely proportional to the distance from the chart.

Clinically, a level of VA specified as 6/6 (meters) or 20/20 (feet) is considered a good normal vision. There are drawbacks to directly measuring VA as described above, however.

Typically, VA must be measured using an eye chart, with the aid of a clinician (such as an Optometrist or an Ophthalmologist), who instructs the subject to read a specific line of the eye chart and then evaluates the subject's response. In the clinic, the clinician's task is to find the prescription by seeking the best optical solution, spherical and astigmatic, that corrects the optical error and minimizes the blur of the visual image on the retina. This best correction, usually referred to as "Rx", includes the spherical power in diopters and, if needed, the cylindrical power and its angle (between 0-180).

The eye can be described as an optical device designed to project an image on the retina. The retina acts as an encoding system that transforms the image into digitized local information (pixels), which are then transferred to the brain. The real process of vision in fact takes place in the brain. The visual processing in the brain decodes the retinal information and performs an interpretation of the best possible solution. This process involves perception and recognition of the visual information. The clinician relies on the patient's subjective reports regarding the recognition of the presented optotypes (i.e., shapes). However, there is larger variability arising from this self-reporting that relies on personal criteria of each individual. Thus, the final prescribed optical correction (Rx), which should bring the image to be sharp on the retina, relies on the subjective patient's reports. However, even after the best achievable optical correction using such standard methods, still there might be cases in which the image is not clear enough due to distortions, optical aberrations, etc. Therefore, often even the best optical correction may pose processing load and inconvenience in the task of perceiving and recognition of the retinal image, resulting in user's discomfort. This can explain the many cases of patients who are unsatisfied with their optical correction. Moreover, there are several factors that affect the way the subject processes the visual image in the brain. Thus, the final outcome of the quality of vision is affected by the optical error and individual brain processing.

It is therefore clear that it would be highly desirable to be able to directly test the level of perception and recognition of the subject during VA evaluation, in order to achieve optimal and comfortable functional vision. It is a purpose of the invention to provide a method that allows to find the best optical correction that will provide the subject the optimal comfortable and sharp vision. It is another object of the invention to provide a VA evaluation process that is fast, accurate and convenient. Other objects and advantages of the invention will become apparent from the following description.

SUMMARY OF THE INVENTION

In one aspect, the invention is directed to a method for measuring an optical error of a subject, comprising displaying to said subject stimuli comprising different levels of blurring. According to one embodiment, the stimuli comprise pairs of images with different blurring levels. According to another embodiment, one of the images in the pair is not blurred.

The stimuli may comprise images having essentially circular, elliptic or square shapes, but are not limited to any specific shape and may also include different, less regular shapes. In one embodiment the stimuli do not comprise letters or numbers. An illustrative but not limitative examples of dimension of the shape is between 0.5 minutes of arc and 60 arcminutes. In one embodiment the contrast between the foreground and background of the stimulus is between 0.1 percent and 100 percent. In another embodiment the stimuli do not comprise letters or numbers.

According to one embodiment the visual capabilities tested include myopia, hyperopia or astigmatism. In another specific embodiment, when the visual capabilities tested is astigmatism, the stimuli used include elliptical blurred images having different orientation. The stimuli can be shown with different presentation times, e.g., 10-500 ms.

In one embodiment the optical errors determined includes at least one of SPH, CYL, AX, ADD. In another embodiment the stimuli used to determine the CYL/level of astigmatism or Axis components of the optical error comprises elliptical blurred images. In a further embodiment the elliptical blurred images are displayed with different orientations.

Also encompassed by the invention is a system for measuring an optical error of a subject, comprising apparatus adapted to display to said subject stimuli comprising different levels of blurring, data collection apparatus suitable to collect the responses of said subject to stimuli presented to him, a database comprising test results of users with different optical errors, who were tested with different parameters, resulting in a detailed correlation between the optical error and the optimal blur discrimination, and logic means adapted to compare between the responses of the subject with the data contained in said database.

In one embodiment the system comprises:
a) Display apparatus
b) Computer program to instruct display to present Stimuli sets with blurred images (displayed as pairs, or sequentially)
c) Data collection apparatus to collect subject responses
d) Computer program to determine optical error from subject responses
In another embodiment the system further comprises
e) A database comprising test results and/or correlations related thereto;
f) A computer program suitable to operate the steps according to the method.

BRIEF DESCRIPTION OF THE DRAWINGS

In the drawings:

FIG. 5(a) is an example of a stimulus with different sizes to test blur discrimination according to invention, and FIG. 5(b) is another example of a stimulus according to the invention, with a larger blurred zone;

FIG. 11 is an example of a target used to measure the astigmatic error according to the invention. The user's task is to report which image is more blurred, FIG. 11(a) being blurred, while FIG. 11(b) is not blurred.

DETAILED DESCRIPTION OF THE INVENTION

Eye and Brain

As mentioned above, the eye can be described as an optical device aiming to project an image onto the retina. The retina acts as an encoding system that transforms the image to digitized local information (pixels) that are subsequently transferred to the brain. In fact, the 'true' process of vision takes place in the brain. About 50% of the cortical area is involved in vision. The purpose of visual processing is to decode the retinal information and to perform an interpretation of the best possible solution, i.e., the interpretation that is the closest to the user's subjective perception. This process involves perception and recognition of the visual information, conditions that capture the real functional vision and not only the quality of the optical correction. Therefore, in many circumstances, even the best optical correction may pose a high processing load and an inconvenience in the task of perception and recognition of the retinal image. According to the invention, the level of perception and recognition is directly tested, in order to afford optimal and comfortable functional vision after appropriate correction.

Blur Perception Properties as a Measure for Visual Acuity

Retinal defocus results in a blurred input to the visual cortex, which in turn results in weaker and slower neuronal responses, with a consequent blurred perception, a reduction in near visual acuity (VA) and contrast sensitivity (Owsley, 2011; Owsley, Sekuler, & Siemsen, 1983; Polat, 2009; Polat et al., 2012). By examining blur perception in terms of detection and discrimination thresholds, we can obtain an indirect measure of visual acuity, which is useful for a more accurate estimation of corrective prescription. According to the invention, the subject is presented with a set of stimuli, identical except for their respective blurs, and the subject's task is to identify the higher blurred stimulus. This is illustrated in FIG. 5, in which pairs of blurred and non-blurred targets are shown with different sizes (FIG. 5 (a)), and in FIG. 5 (b) a pair is shown with a greater relative blurring. In this example, the blur is achieved by convolution of a sharp circle (or any other image) by Gaussian or similar convolution operations. Different blur sizes can be achieved by changing the standard deviation of the Gaussian (size).

Figure 1:
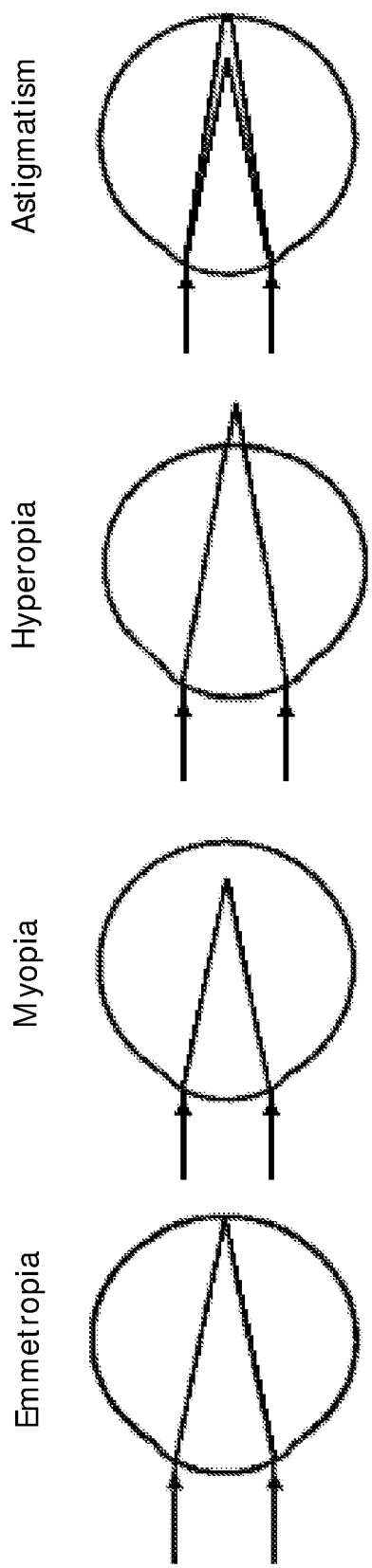
FIG. 1 schematically illustrates three principal refractive errors.
Figure 2:
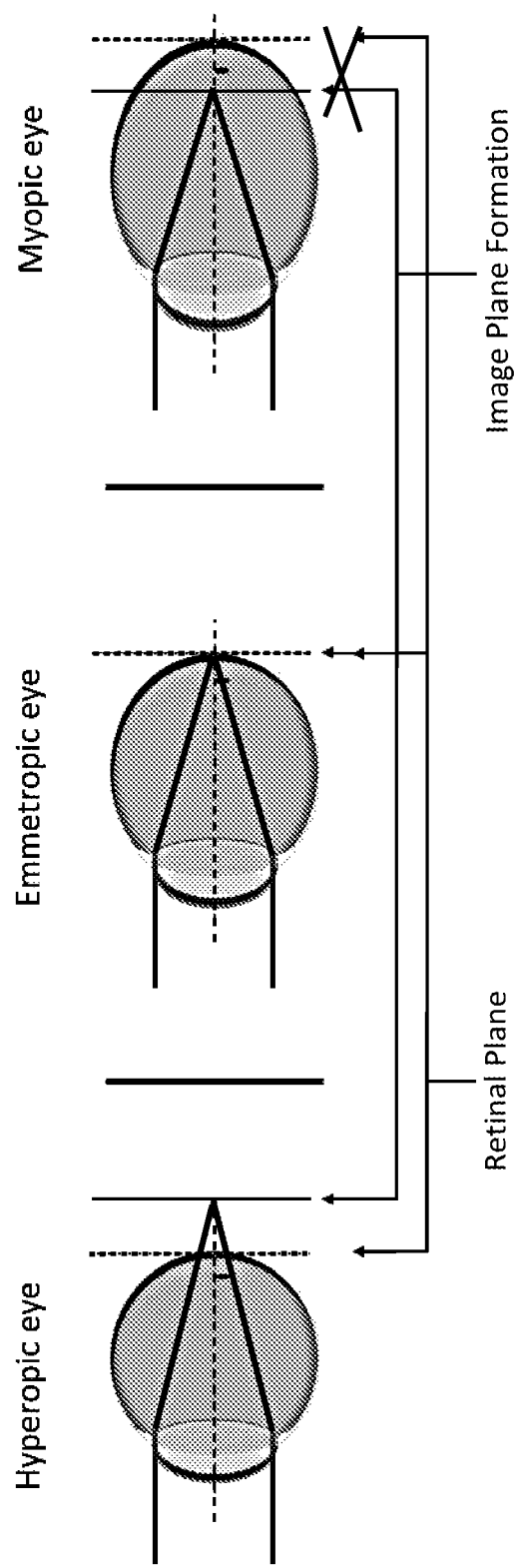
FIG. 2 schematically illustrates the blurred zone resulting on the retinal plane in cases of optical error such as myopia or hyperopia.
Figure 3:
FIG. 3 shows examples of common charts used in the clinics to test visual acuity.
Figure 4:
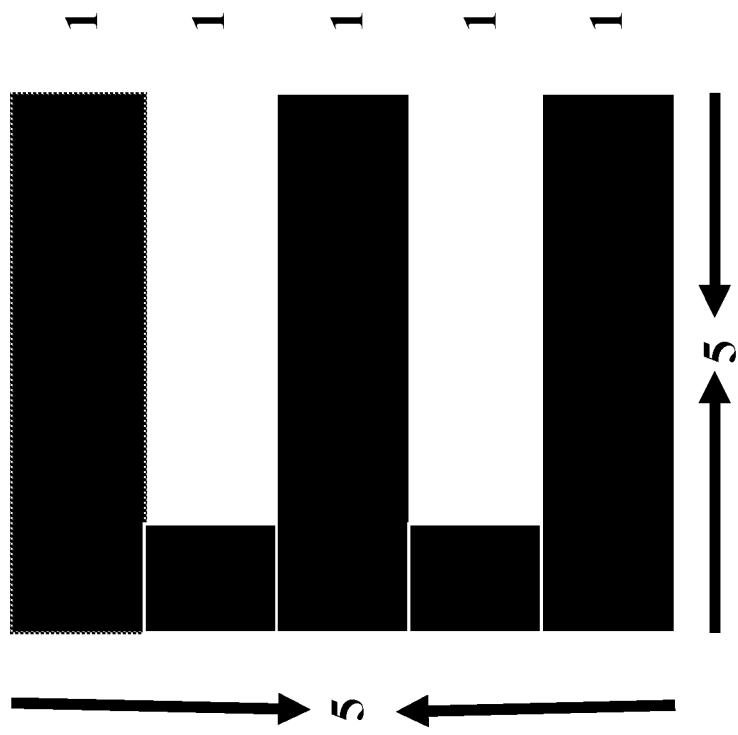
FIG. 4 shows an example of an optotype letter used to test visual acuity.
Figure 6:
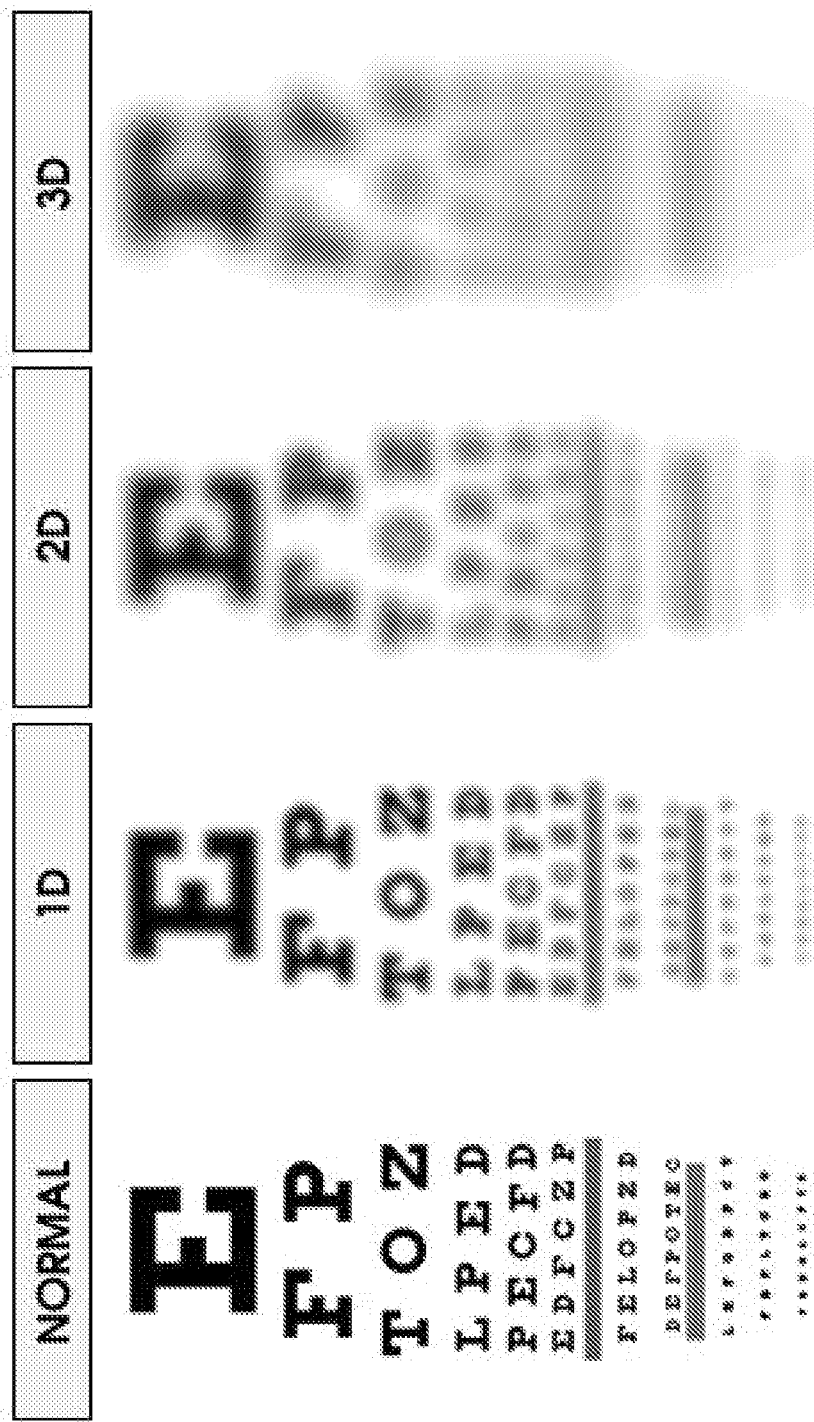
FIG. 6 illustrates how in optical error causes the optotype to look "blurred", the higher the optical error in diopter (D) results in more blur.

Before the invention, blur perception tests have been routinely carried out using letters, lines or other objects, which the inventors have found that contributed to the large variability in the resulting corrective prescription. Moreover, classic VA measurement is carried out by identifying the minimal gap that the patient can see, relying on the assumption that it is limited by the blur dimensions. For example, larger optical errors in diopter cause larger blur on the letter size, as illustrated in FIG. 6, which shows how a chart would look to a subject with a 6/6 vision and two subjects with 1, 2, and 3 diopters.

Figure 7:
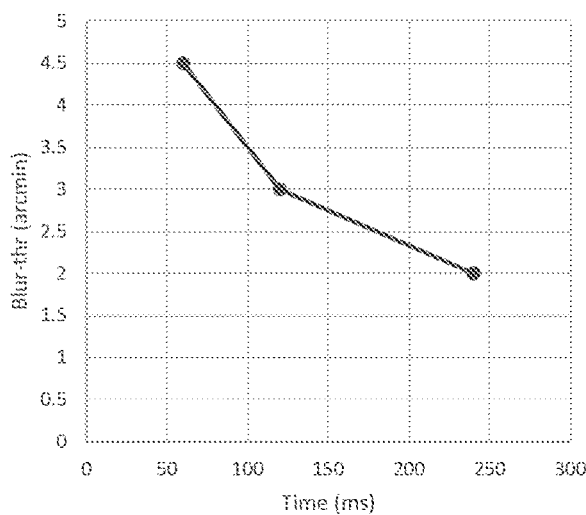
FIG. 7(a) is an example of the correlation between blur threshold and the presentation time, showing that increasing presentation time improve the blur discrimination.
FIG. 7(b) shows that increasing the image size improves also the percent correct of identify blur (number of true answers correctly identifying the target) divided by the number of presentations.
FIG. 7(c) shows that the same improvement can also be achieved by increasing the contrast of the target.
Figure 7:
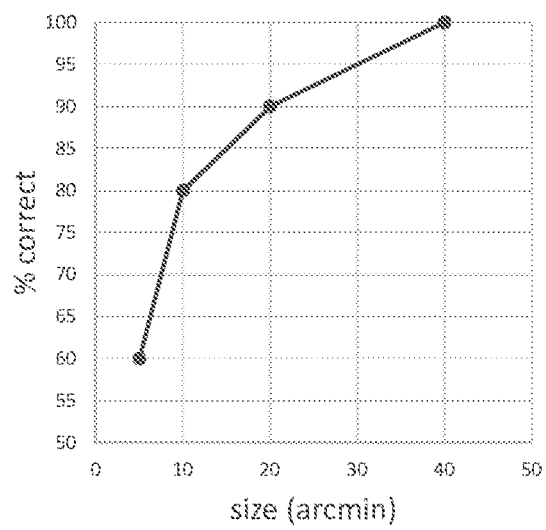
Figure 7:
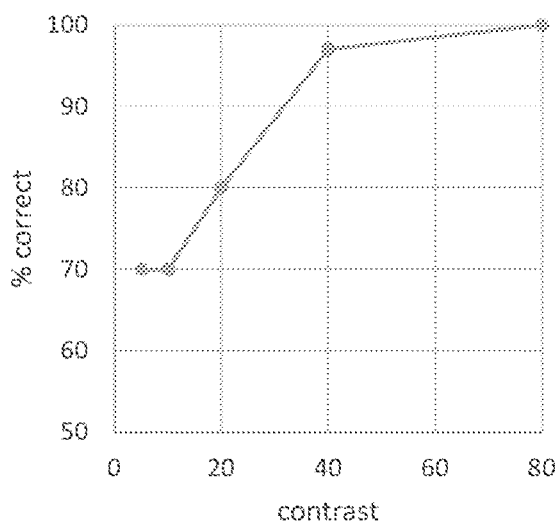

The invention employs a novel set of stimuli, which overcome the subjective variability of the perception of sharpness. The set of stimuli includes images with different sizes, each size with different blur size, different contrasts. Each image can be presented for different presentation time. In this case, the stimuli do not contain cues of sharpness, contrast, shape, size or edges, as can be clearly seen from the example of FIG. 5. The invention provides good and direct estimation of the user's prescription from the blur discrimination. This is made possible by the invention, because it relies on directly testing how the subject perceives blurred image that are projected on a monitor or other display, and fall on the retina. The reports are measured through response devices and thereby the invention allows the determination of the most accurate optical error, which causes the blurred image on the retina. According to the invention it is possible to analyze situations in which the perceived blur is affected by several parameters. After each response given by the user, the algorithm calculates if there is enough reliable data to reach a decision. If the decision is that the user makes too many errors, a new set of images that are supposed to be easier for the user is provided. If the decision is that the responses indicated "too easy", a next step will be testing a more difficult set. This process will continue until a determination that the user reached the threshold level, meaning that he cannot respond better or worse, and this is the optimal image for him. Thus, the current test involves multi-parameter testing of the target, including several levels of contrasts, size and presentation time. it was surprisingly found that a strong relationships exists between the blur perception and presentation time, contrast and stimuli size, as illustrated in FIG. 7 (*a-c*). Thus, according to the invention it is possible to rely on large data set that extract the best Rx from the database that optimally match with the user's responses. The database is composed of many test results of users with different optical errors, who were tested with different parameters, resulting in a detailed correlation between the optical error and the optimal blur discrimination. Testing included are those performed for different ages of users, different conditions (myopia, presbyopia, amblyopia etc). The database includes also information about sphering optical error alone or combined with astigmatic error. The skilled person will easily fill information in the database, according to the guidance provided herein.

Testing subjects with a large number of variable parameters is time consuming and cumbersome, and renders it less practical for commercial use. For example, in cases such as low myopia, the best parameter that may be correlated with the Rx is a low contrast level of the target. However, for subjects with high Rx, the best parameter may be a high contrast. As clearly seen in FIG. 8 the blur size shows a linear correlation of the blur size with the required Rx as prescribed by an Optometrist. Each data point denotes an example of one user with different optical error (diopter) as shown in the x axis. Thus, users with higher diopters have a higher blur size. So the dashed diagonal line describes the relationships (correlation) between the diopters and the blur size. In the case shown, the correlation is very high ($r^2=0.9158$), meaning that R=0.956, and can explain more than 95% of the error, hence the measure is very reliable.

Figure 8:
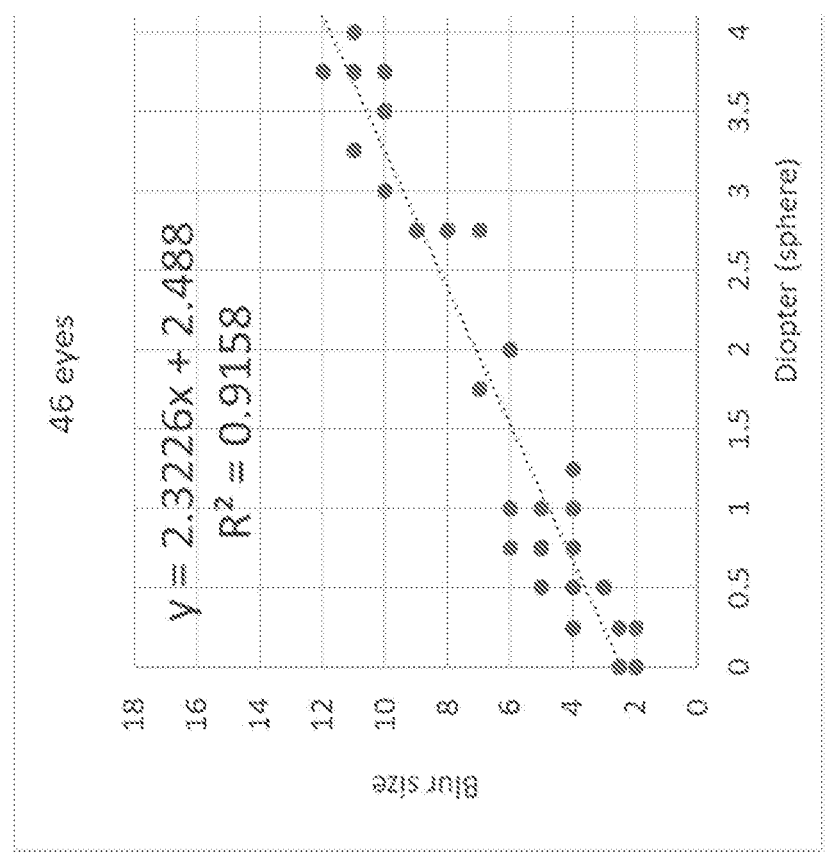
FIG. 8 is an example of a correlation between blur size (Y axis) and optical error in diopters (X axis), each data point representing one eye, the dashed line showing a linear correlation with strong relationships between the blur discrimination and the optical error of the eye.

The invention permits to shorten the testing time based on a real-time analysis of the subject's response, which is then compared with the database. To reach this goal, an adaptive psychophysical procedure was developed, which allows for a quick estimation of the blur discrimination threshold (i.e., the limit of discriminating between blurred and not blurred images), as shown in FIG. 8.

Figure 9:
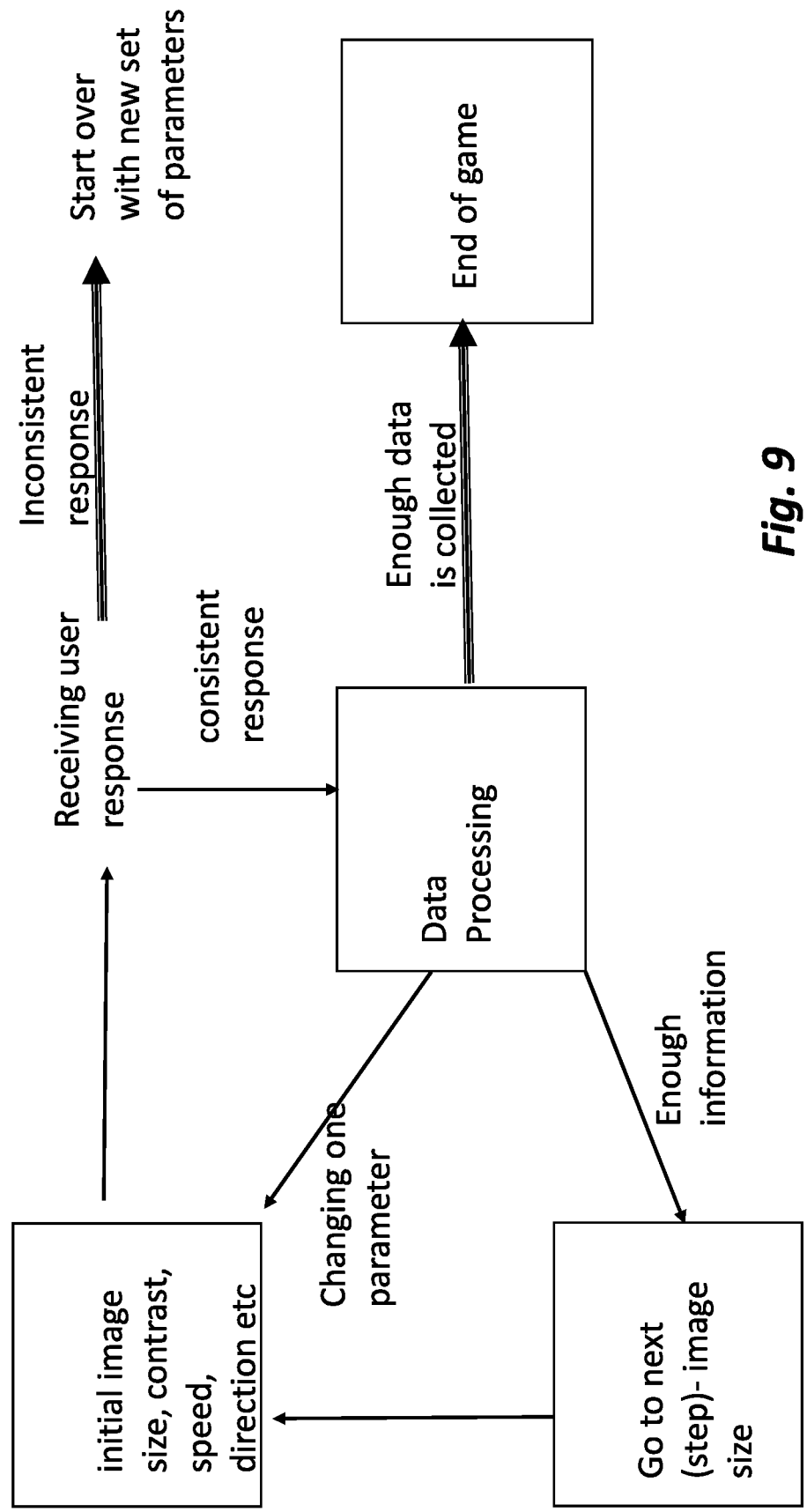
FIG. 9 is a block diagram describing the testing process.
Figure 10:
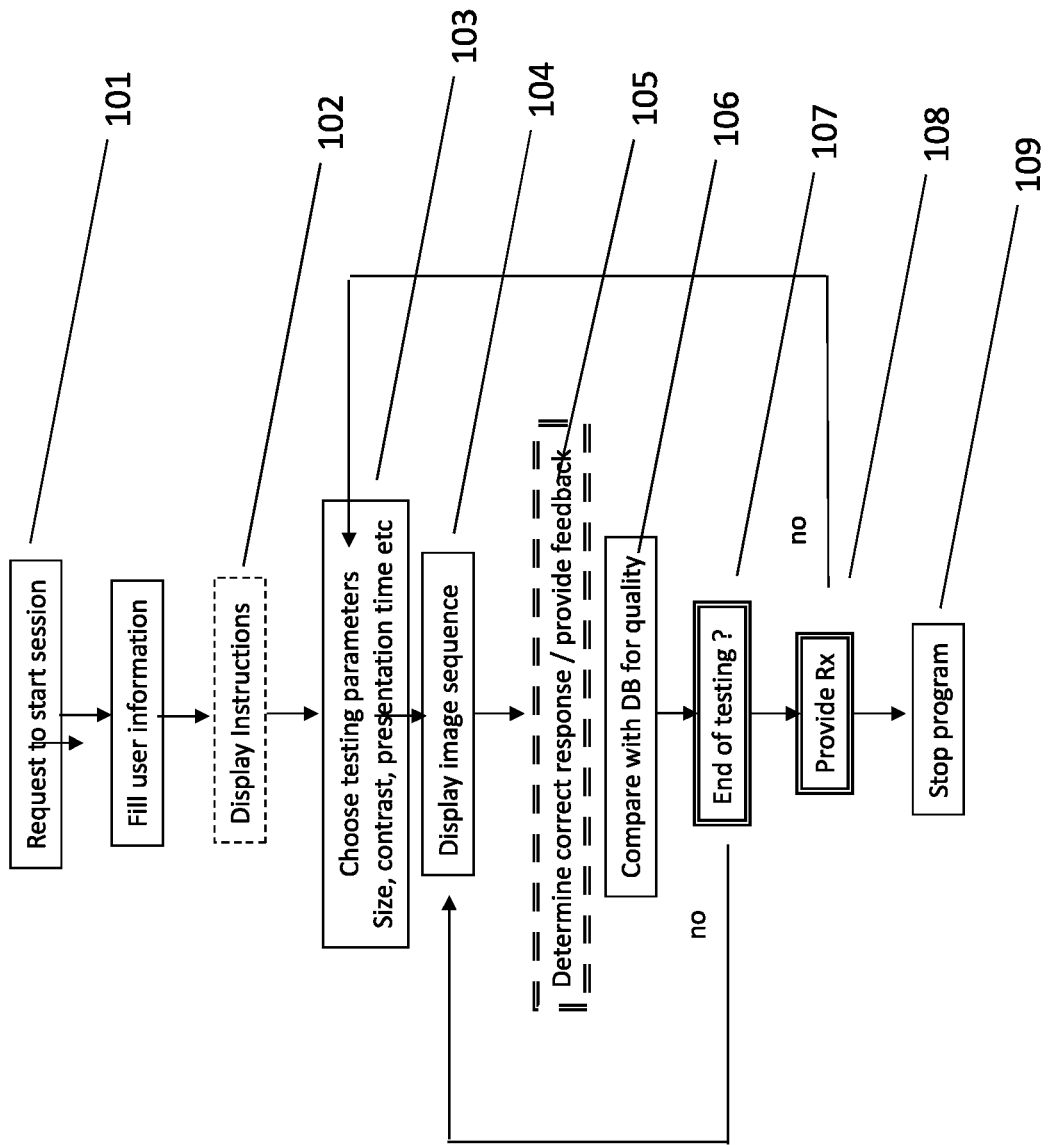
FIG. 10 is a block diagram describing the testing flow, step-by-step.

The following procedures illustrate the invention:

Estimating the sphere: according to the invention, the spherical power is measured by presenting targets with different blurred size, target size, presentation time and contrast, as schematically shown in FIG. 5. The subject's task is to indicate if the target is blurred or not. This can be achieved through a discrimination task, in which the user needs to compare between two images and indicate which one is more blurred. In other option is to present only one image, and ask the user to indicate if the target is blurred or not. The response is stored and compared with the data base. The task can be repeated until a decision that reliable data is achieved is made, by comparing it with the database and determining whether there is a sufficient number of correct responses to make a decision. FIG. 9 describes the various elements of the process. In FIG. 10, the steps of the process are detailed. Step 101 initiate the session and is followed by a "housekeeping step" (not numbered) in which user information are fed to the system. In step 102 instructions are displayed to the user (for instance, instructions on how to make fixation, which button should the user push for correct response, etc. This is a user interference issue that can be adjusted to the device that is being used). Step 103 is the step in which appropriate stimuli are selected. In step 104 the selected image sequences are displayed to the subject. In Step 105 the subject's responses analyzed. In Step 106 the subject's response is compared with the database to determine its quality and the output of this step determines whether the test meets the requirements and is ended in Step 107. If the obtained quality is not satisfactory (as determined and updated over time, which may be different for different presentation sets), the process returns to Step 104. If the test ends, the Rx can be provided in Step 108 and the process ends in Step 109. The process cycles back from step 108 to step 103 when there is not enough reliable information to end the process.

Figure 11:
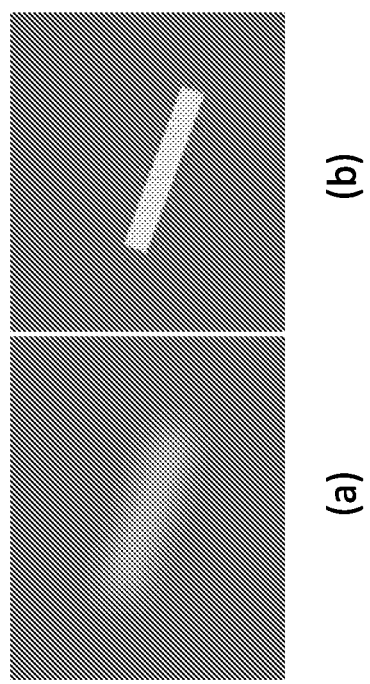

Estimating the astigmatic axis and power. As mentioned above, the optical error may include astigmatic error. In astigmatic error, there is an axis with higher optical power (higher diopter) which causes a higher blurred zone on the retina. Unlike the spherical error, which produces circular blurred image on the retina, the astigmatic zone appears as an elliptical blur on the retina (Cholewiak, Love, & Banks, 2018). There are two elliptical zones on the retina, and the one with the higher optical error will appear as more blurred. The other one, on the orthogonal axis, will show a lower blur. Thus, according to the invention the elliptical blurred zone is directly measured on the retina, using a stimulus as the one shown in FIG. 11. Rather than performing a Gaussian convolution on circular shape, for astigmatic testing the convolution is performed on an elliptical shape. The size of the ellipse and its blur is directly correlated with the astigmatic power. Thus, in this case the used parameters are the ellipse size and blur size.

In order to find the blurred axis, the invention employs elliptical blurred images having different axis (orientation), with different contrast and presentation time, asking the user to report about the most blurred elliptical image. This task is repeated until the collected data indicated that the user reliably reports on the blurred orientation. After finding the cylindrical axis, the procedure to find the blur size (power) is performed. In this task, the user is presented with elongated blurred image, such as that shown in FIG. 11, oriented in the blurred axis, and is asked to report about the blur discrimination or perception. This can be done, for example, by comparing between two images with different blurred size, at the same orientation and location. Alternatively, one can test the blur by comparing between the cylindrical axis and the orthogonal axis. The procedure is repeated until reliable data is achieved.

Final prescription: in order to find the final prescription for Eyewear/spectacle correction (Rx), the spherical blurred image is combined with the elliptical image, producing an elongated image with blurred zones, and a fine tuning of the best and lower blurred image that the user perceives is performed. This includes the spherical power, and if needed, the astigmatic power with its axis. The final prescription is equivalent (i.e., comparable and similar) with the Rx prescribed by a certified clinician.

BIBLIOGRAPHY

Cholewiak, S. A., Love, G. D., & Banks, M. S. (2018). Creating correct blur and its effect on accommodation. *J Vis*, 18(9), 1. doi:10.1167/18.9.1

Del Aguila-Carrasco, A. J., Esteve-Taboada, J. J., Papadatou, E., Ferrer-Blasco, T., & Montes-Mico, R. (2017). Amplitude, Latency, and Peak Velocity in Accommodation and Disaccommodation Dynamics. *Biomed Research International*, 2017, 2735969. doi:10.1155/2017/2735969

Owsley, C. (2011). Aging and vision. *Vision Res*, 51(13), 1610-1622. doi:10.1016/j.visres.2010.10.020

Owsley, C., Sekuler, R., & Siemsen, D. (1983). Contrast sensitivity throughout adulthood. *Vision Res*, 23(7), 689-699.

Polat, U. (2009). Making perceptual learning practical to improve visual functions. *Vision Res*, 49(21), 2566-2573. doi:10.1016/j.visres.2009.06.005

Polat, U., Schor, C., Tong, J. L., Zomet, A., Lev, M., Yehezkel, O., . . . Levi, D. M. (2012). Training the brain to overcome the effect of aging on the human eye. *Sci Rep*, 2, 278. doi:10.1038/srep00278

The invention claimed is:

1. A method for determining an optical error of a subject, comprising displaying stimuli with an induced blur by:
 a) choosing testing parameters being adapted to optical parameters of said subject;
 b) displaying to said subject, a sequence of images that correspond to the chosen testing parameters;
 c) collecting data related to said subject responses;
 d) analyzing said collected data;
 e) comparing said data with a database to determine its quality and if the test meets the requirements;
 f) determining the optical error of said subject; and
 g) providing prescription for said subject's eyewear according to said optical error,
 wherein said database comprises test results of different subjects with correlation between their optical error and the optimal blur discrimination.

2. A method according to claim 1, wherein one stimulus is displayed and the patient is instructed to determine whether it is blurred, and the patient's response comprises the patient's determination.

3. A method according to claim 1, wherein two stimuli are displayed and the patient is instructed to determine which of said two stimuli has a higher (or lower) level of blur, and the patient's response comprises the patient's determination.

4. A method according to claim 3 wherein the patient's responses are used to determine the blur discrimination threshold of the patient.

5. A method according to claim 1, wherein the stimuli comprise pairs of images with different levels of blur.

6. A method according to claim 1, wherein the stimuli comprises pairs of images with different levels of blur displayed sequentially.

7. A method according to claim 5, wherein one of the images in the pair is not blurred.

8. A method according to claim 1, wherein the stimuli comprises images having essentially circular, elliptic or square shapes.

9. A method according to claim 8, wherein the dimension of the shape is between 0.5 minutes of arc and 60 arc-minutes.

10. A method according to claim 8, wherein the contrast between the foreground and background of the stimulus is between 0.1 percent and 100 percent.

11. A method according to claim 1, wherein the stimuli do not comprise letters or numbers.

12. A method according to claim 1, wherein the optical errors determined includes at least one of SPH, CYL, AX, ADD.

13. A method according to claim 12, wherein the stimuli used to determine the CYL/level of astigmatism or Axis components of the optical error comprises elongated blurred images.

14. A method according to claim 13, wherein said elongated blurred images are displayed with different orientations.

15. A method according to claim 1, further comprising, in case the obtained quality of said data is not satisfactory, and before determining the optical error of said subject:
 a) choosing different testing parameters; and
 b) displaying to said subject a sequence of images that correspond to said different testing parameters.

16. A system for determining an optical error of a subject, comprising:
 a) an apparatus adapted to display to said subject stimuli comprising blurred images by:
  a.1) choosing testing parameters being adapted to optical parameters of said subject;
  a.2) displaying to said subject, a sequence of images that correspond to the chosen testing parameters;
  a.3) collecting data related to said subject responses;
  a.4) analyzing said collected data;
  a.5) comparing said data with a database to determine its quality and if the test meets the requirements;
  a.6) determining the optical error of said subject; and
  a.7) providing prescription for said subject's eyewear according to said optical error, b) a data collection apparatus suitable to collect the responses of said subject to stimuli presented to said subject; and
 c) a database comprising test results of users with different optical errors, who were tested with different parameters, resulting in a detailed correlation between the optical error and the optimal blur discrimination, and logic means adapted to compare between the responses of the subject with the data contained in said database.

17. A system according to claim 16, wherein the system comprises: g) Display apparatus h) Computer program to instruct display to present Stimuli sets with blurred images (displayed as pairs, or sequentially) i) Data collection apparatus to collect subject responses j) Computer program to determine optical error from subject responses.

18. A system according to claim 17, further comprising;
k) A database comprising test results and/or correlations related thereto;
l) A computer program suitable to operate the steps according to the method.

* * * * *